United States Patent [19]

Diana

[11] 4,451,476
[45] May 29, 1984

[54] ISOXAZOLES AS ANTIVIRAL AGENTS

[75] Inventor: Guy D. Diana, Stephentown, N.Y.

[73] Assignee: Sterling Drug Inc., New York, N.Y.

[21] Appl. No.: 542,871

[22] Filed: Oct. 17, 1983

Related U.S. Application Data

[63] Continuation-in-part of Ser. No. 449,060, Dec. 13, 1982, abandoned.

[51] Int. Cl.$^3$ .................... A61K 31/42; C07D 261/08
[52] U.S. Cl. .................................... 424/272; 548/247
[58] Field of Search ................ 424/272; 548/247, 240

[56] References Cited

U.S. PATENT DOCUMENTS 4,268,678  5/1981  Diana et al. .......................... 548/247

OTHER PUBLICATIONS

Kohler et al., "Nitrocyclopropane Derivatives," *Chem. Abst.*, 13: 2682, (1919).
Kochetkov et al., "Isoxazole Series," *Chem. Abst.*, 55: 18707(f), (1961).
Sokolov et al., "Isoxazole Series," *Chem. Abst.*, 65: 8734(e), (1966).
Yukichi et al., "Acetylenic Compounds," *Chem. Abst.*, 68: 12885(j), (1968).

Belgodere et al., "Ultraviolet Spectra of Styrylisoxazoles," *Chem. Abst.*, 79: 91167(e), (1973).
Carb et al., "Isoxazole Antihelmenthics," *Chem. Abst.*, 87: 15689(b), (1977).
Barber et al., ". . . Synthesis Isoxazoles," *Chem. Abst.*, 89: 75360p, (1978).

*Primary Examiner*—Mary C. Lee
*Assistant Examiner*—G. Hendricks
*Attorney, Agent, or Firm*—Thomas L. Johnson; B. Woodrow Wyatt; Paul E. Dupont

[57] ABSTRACT

Compounds of the formulas:

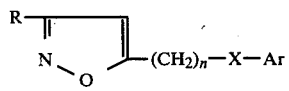

and

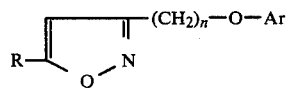

wherein R is alkyl, X is O or $CH_2$, n is an integer from 4 to 8, and Ar is phenyl or substituted phenyl are useful as antiviral agents especially against picornaviruses.

20 Claims, No Drawings

ISOXAZOLES AS ANTIVIRAL AGENTS

This application is a continuation-in-part of application Ser. No. 449,060, filed Dec. 13, 1982 now abandoned.

BACKGROUND OF THE INVENTION

1. Field of the Invention

This invention relates to novel 5-(aryl-aliphatic)-3-lower-alkylisoxazoles and isomers thereof, to the preparation thereof and to compositions and methods for the use thereof as antiviral agents.

2. Information Disclosure Statement

Diana and Carabateas U.S. Pat. No. 4,268,678, issued May 19, 1981, discloses antivirally active compounds having the formula:

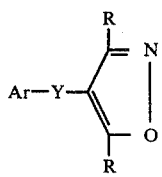

wherein Ar is phenyl substituted by one or two substituents selected from the group consisting of halogen, lower-alkoxy, nitro and hydroxy; Y is $(CH_2)_n$ or $O(CH_2)_n$ where n is an integer from 1 to 8; and R is lower-alkyl. Illustrative specific compounds disclosed in the patent are 4-[4-(2-chloro-4-methoxyphenoxy)-butyl]-3,5-diethylisoxazole, 4-[7-(2-chloro-4-methoxyphenoxy)heptyl]-3,5-diethylisoxazole, and 4-[6-(2-chloro-4-methoxyphenoxy)hexyl]-3,5-diethylisoxazole.

SUMMARY OF THE INVENTION

In a composition of matter aspect, the invention relates to compounds having the formula:

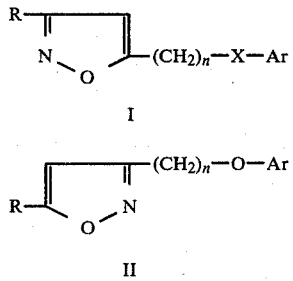

wherein:
R is alkyl of 1 to 3 carbon atoms;
X is O or $CH_2$;
n is an integer from 4 to 8; and
Ar is phenyl or phenyl substituted by one or two substituents selected from the group consisting of halogen, lower-alkyl, lower-alkoxy, nitro, cyano, carboxy, lower-alkoxycarbonyl, lower-alkanoyl, 1-oximino-lower-alkyl, hydrazinocarbonyl, carbamyl and N,N-di-lower-alkylcarbamyl.

In a further composition of matter aspect, the invention relates to compositions for combatting viruses which comprise an antivirally effective amount of at least one compound of the above Formulas I or II in admixture with a suitable carrier or diluent.

In a process aspect, the invention relates to a process for preparing a compound of Formulas I or II which includes the step comprising:

(a) reacting an alkali metal derivative of 3-R-5-methylisoxazole with a compound of the formula

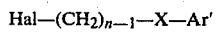

where Hal is bromine or iodine, and Ar' is phenyl or phenyl substituted by one or two substituents selected from the group consisting of halogen, lower-alkyl, lower-alkoxy, nitro and cyano; or (b) reacting a compound of the formula

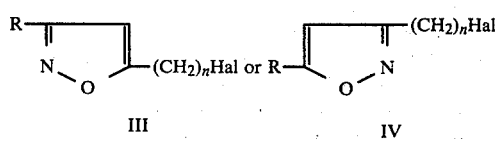

where Hal is bromine or iodine, with an alkali metal salt of a compound of the formula

where Ar' has the meaning given above.

In a further process aspect, the invention relates to a method for combatting viruses which comprises contacting the locus of said viruses with an antivirally effective amount of at least one compound of Formulas I or II.

DETAILED DESCRIPTION INCLUSIVE OF PREFERRED EMBODIMENTS

In the compounds of Formulas I and II, when the phenyl group is substituted by lower-alkyl, lower-alkoxy, lower-alkoxycarbonyl, lower-alkanoyl or di-lower-alkyl-carbamyl, the lower-alkyl moieties preferably have from one to four carbon atoms which can be straight or branched; and when halogen substituents are present they can be any of the four common halogens, fluoro, chloro, bromo or iodo.

A process for the preparation of the compounds of Formula I comprises the alkylation of a 3-R-5-methylisoxazole with an aryl-aliphatic halide, Hal—$(CH_2)_{n-1}$—X—Ar', in the presence of a strong base under essentially anhydrous conditions. The reaction takes place readily in an inert solvent at a temperature below room temperature. A preferred temperature is between $-70°$ and $-30°$ C.; higher temperatures produce color and a lowering of yield. The strong base can be any reagent which forms an alkali metal derivative of the 3-R-5-methylisoxazole and promotes C-alkylation by removal of hydrogen halide, and includes such reagents as alkali metal alkoxides, alkali metal amides, alkali metal hydrides or alkali metal-hydrocarbon compounds such as alkyllithiums. Preferred reagents are N-butyllithium and lithium diisopropylamide.

The foregoing process is effective to produce compounds of Formula I wherein Ar is phenyl or phenyl substituted by halogen, lower-alkyl, lower-alkoxy or cyano. The compounds where Ar is substituted by carboxy, lower-alkoxy-carbonyl, lower-alkanoyl, hydrazinocarbonyl or carbamyl cannot effectively be produced directly by the primary process either because of failure of the reaction to take place or because of competing side-reactions. One exception is a compound where Ar is substituted by tertiary-butyloxycarbonyl which was prepared in low yield by the primary process. Instead, the compounds where Ar is substituted by carboxy, lower-alkoxycarbonyl, lower-alkanoyl, 1-oximino-lower-alkyl, hydrazinocarbonyl, carbamyl or N,N-di-lower-alkylcarbamyl were prepared from the respective compounds where Ar is substituted by cyano as follows:

Acid hydrolysis of the cyano compounds provided the corresponding carboxy compounds which were then esterified by conventional procedures to give the lower-alkoxy-carbonyl substituted compounds. Mild alkaline hydrolysis of the cyano compounds provided the corresponding amides where cyano is replaced by carbamyl.

The N,N-di-lower-alkylcarbamyl group was formed by reacting the acid chloride of a carboxy substituted compound with a di-lower-alkylamine.

The compounds of Formula I where Ar is substituted by lower-alkanoyl were prepared by reacting the corresponding cyano compounds with a lower-alkylmagnesium halide in a conventional Grignard reaction. Oxime formation with hydroxylamine afforded the 1-oximino-lower-alkyl compounds.

The hydrazinocarbonyl group was formed by reacting the corresponding alkoxycarbonyl compound with hydrazine in a conventional amidation reaction.

The intermediate aryl-aliphatic halides, Hal—$(CH_2)_n$—X—Ar' are known classes of compounds. The intermediates where X is O are prepared by reacting a dihalide, Hal—$(CH_2)_{n-1}$—Hal, with an alkali metal salt of a phenol, HOAr', as described in U.S. Pat. No. 4,031,246. The intermediates where X is $CH_2$ are prepared by procedures analogous to those shown in U.S. Pat. No. 4,093,726 starting with the appropriate aldehyde Ar'CHO and methyl cyclopropyl ketone, and following the reaction sequence A of said patent.

The compounds of Formula I where X=O can also be prepared by reacting a 3-R-5-haloalkylisoxazole of Formula III with an alkali metal salt of a phenol, HOAr'. The reaction is carried out by heating the substituted isoxazole and the phenol with an alkali metal base such as potassium carbonate in an inert solvent. The intermediate of Formula III is in turn prepared by reacting an alkali metal derivative of a 3-R-5-methylisoxazole with a dihalide, Hal—$(CH_2)_{n-1}$—Hal.

The compounds of Formula II are similarly prepared by reacting a 5-R-3-haloalkylisoxazole of Formula IV with an alkali metal salt of a phenol, HOAr'. The compounds of Formula IV are in turn prepared by a reaction sequence involving conventional side-chain homologation reactions starting with a 5-R-isoxazole-3-carboxylic acid. This is illustrated by the procedures described hereafter in Example 40.

The structures of the compounds of the invention were established by the modes of synthesis, by elementary analysis, and by infrared and nuclear magnetic resonance spectral determinations.

The compounds of Formulas I and II are useful as antiviral agents or as intermediates for other compounds of Formulas I and II having antiviral activity.

The in vitro testing of the compounds of the invention against rhinovirus showed that they inhibited viral growth at minimum concentrations (MIC) ranging from about 0.04 to about 25 micrograms per milliliter. The MIC values were determined by standard serial dilution procedures. Extensive testing of a preferred compound, 5-[7-(2-chloro-4-methoxyphenoxy)heptyl]-3-methylisoxazole, demonstrated in vitro activity against a variety of picornaviruses and enteroviruses, including numerous strains of rhinoviruses and polioviruses, as well as in vivo activity against poliovirus infections in mice.

The antiviral compositions are formulated for use by preparing a dilute solution or suspension in a pharmceutically acceptable aqueous, organic or aqueous-organic medium for parenteral administration by intravenous or intramuscular injection, or for intranasal or ophthalmic application; or are prepared in tablet or capsule form with conventional excipients for oral administration.

The following examples will further illustrate the invention.

EXAMPLE 1

5-[7-(2-Chloro-4-methoxyphenoxy)heptyl]-3-methylisoxazole

[I; R is $CH_3$, n is 7, X is O, Ar is 2—Cl—4—$CH_3OC_6H_3$].

To a mixture of 2.91 g (0.03 mole) of 3,5-dimethylisoxazole in 70 ml of dry tetrahydrofuran cooled to −70° C. was added 18.8 ml (0.03 mole) of n-butyllithium (1.55 molar in hexane) and 9.6 g (0.03 mole) of 6-(2-chloro-4-methoxyphenoxy)hexyl bromide in 3 ml of tetrahydrofuran. An additional 10 ml of tetrahydrofuran was added and the reaction mixture was stirred at −65° C. for one hour. The reaction mixture was then allowed to warm to room temperature, kept there for two days, and then concentrated in vacuo to give 22 g of orange oil. The latter was partitioned between 80 ml of 5% ammonium chloride solution and 100 ml of ether. The aqueous layer was extracted twice with 80 ml of ether, and the combined ether layers were dried over anhydrous magnesium sulfate and concentrated in vacuo. The residue was dissolved in 100 ml of absolute ether and chromatographed on a column containing 300 g of aluminum oxide. The column was eluted with hexane (Skellysolve B) containing increasing amounts of ether. Eluants containing 20–40% ether brought out 6.0 g of the desired product 5-[7-(2-chloro-4-methoxyphenoxy)heptyl]-3-methylisoxazole, m.p. 45°–46° C.

The intermediate 6-(2-chloro-4-methoxyphenoxy)hexyl bromide was prepared from the potassium salt of 2-chloro-4-methoxyphenol and 1,6-dibromohexane in accordance with Example 2 of U.S. Pat. No. 4,031,246.

EXAMPLE 2

5-[7-(2-Chloro-4-methoxyphenoxy)heptyl]-3-methylisoxazole

Lithium wire (3.5 g, 0.5 mole) was washed free of oil in hexane and cut into approximately 5 mm lengths which were stored under tetrahydrofuran pending addition to the reaction vessel. The reaction was carried out in a 1 liter flask equipped with a nitrogen inlet, a thermometer and a pressure equalizing addition funnel. Dry tetrahydrofuran (125 ml) was put into the flask, a nitrogen cover established and the lithium wire added. Diisopropylamine (77 ml, 0.55 mole) was added all at once and at an internal temperature maintained at 20°–25° C. styrene (40 ml, 0.35 mole) was added dropwise over a 2 hour period. When the addition had been completed the mixture was stirred at ambient temperature until all the lithium had been consumed (about 2 hours).

The reaction mixture containing lithium diisopropylamide was cooled in a Dry Ice-isopropanol bath to −55° C. and maintained at −55°±5° during the addition over 15 minutes of 50 g (0.5 mole) of 3,5-dimethylisoxazole and for a one hour stirring period. An additional 125 ml of tetrahydrofuran was added slowly to prevent an increase in the temperature. With the temperature maintained at the −55°±5° C. range the addition of 166 g (0.5 mole) of 1-(6-bromohexyloxy)-2-chloro-4-methoxybenzene (recrystallized from methanol) was commenced. The reaction was quite exothermic and required about 45 minutes to complete the addition without allowing the temperature to rise above −30° C. After the addition was finished the mixture was stirred overnight at ambient temperature. The reaction mixture was concentrated in vacuo to an amber oil which was taken up in 700 ml of 5% aqueous ammonium chloride and 750 ml of ethyl ether. The organic layer was separated and the aqueous layer was extracted twice with ether (300 ml, 200 ml). The combined organic solutions were washed with 400 ml of water, then with 300 ml of brine and dried over anhydrous magnesium sulfate.

After filtration to remove the drying agent, the filtrate was concentrated on a rotary evaporator to give a light amber oil weighing 190 g which crystallized upon standing. The crystalline residue was taken up in 380 ml of ethyl ether and diluted with 380 ml of hexane. The solution was cooled and the solid which crystallized was separated by filtration, and the cake was washed with 200 ml of 1:1 ether-hexane. The air-dried solid weighed 101.6 g (60% of theory). The liquor was concentrated again leaving 82 g of oil. It was taken up in 125 ml ethyl ether, diluted with 165 ml hexane and a second crop was obtained weighing 28.3 g (16.8% of theory). The 129.9 g of 5-[7-(2-chloro-4-methoxyphenoxy)heptyl]-3-methylisoxazole thus obtained had a melting range 45°–46° C. after drying in a vacuum chamber at room temperature, and was identical with the compound obtained in Example 1.

A further 20% of product could be obtained from the mother liquors by allowing the stripped residue to be adsorbed on a pad of Silica 7G (Baker reagent containing 13% calcium sulfate hemihydrate) held on a suction filter, and eluting the pad first with hexane and then with hexane-ether 5:1. The hexane contained starting material (bromo-ether) and the hexane-ether contained final product.

In vitro studies revealed that 5-[7-(2-chloro-4-methoxyphenoxy)heptyl]-3-methylisoxazole was active (MIC=0.01 to 5.8 μg/ml) against 24 of 27 human rhinovirus serotypes (six of the seven most common serotypes). It was also active against other picornaviruses and enteroviruses, and MIC values of 0.15, 0.04, 0.15 and 0.08 μg/ml were found for Echo-9, Echo-11, Polio-2 and Polio-3, respectively.

5-[7-(2-Chloro-4-methoxyphenoxy)heptyl]-3-methylisoxazole was also active in vivo. Mice were infected intracebrally with a lethal dose of poliovirus and orally medicated for 14 days with placebo corn oil or the test compound solubilized in corn oil. The results showed that said compound had a minimal inhibitory dose of 31 mg/kg b.i.d. Parenteral medication with the compound prevented death in mice infected with challenge doses of poliovirus as high as 200 LD$_{50}$.

5-[7-(2-Chloro-4-methoxyphenoxy)heptyl]-3-methylisoxazole was found to be at least 15 times as active in vitro against rhinovirus Type 2 as the corresponding 2-chloro-4-methoxyphenoxy compounds of U.S. Pat. No. 4,268,678.

The following Examples 3–13 were prepared by procedures analogous to the procedure described above in Example 1.

EXAMPLE 3

5-[6-(2-Chloro-4-methoxyphenoxy)hexyl]-3-methylisoxazole

[I; R is CH$_3$, n is 6, X is O, Ar is 2—Cl—4—CH$_3$OC$_6$H], colorless clear liquid, in 53% yield from 3,5-dimethylisoxazole and 5-(2-chloro-4-methoxyphenoxy)pentyl bromide; MIC vs. rhinovirus Type 2 in vitro=0.8 μg/ml.

The intermediate 5-(2-chloro-4-methoxyphenoxy)pentyl bromide was prepared from the potassium salt of 2-chloro-4-methoxyphenol and 1,5-dibromopentane.

EXAMPLE 4

5-[5-(2-Chloro-4-methoxyphenoxy)pentyl]-3-methylisoxazole

[I; R is CH$_3$, n is 5, X is O, Ar is 2—Cl—4—CH$_3$OC$_6$H$_3$], m.p. 38° C., in 65% yield from 3,5-dimethylisoxazole and 4-(2-chloro-4-methoxyphenoxy)butyl bromide; MIC vs. rhinovirus Type 2 in vitro=0.4 μg/ml.

The intermediate 4-(2-chloro-4-methoxyphenoxy)butyl bromide was prepared from the potassium salt of 2-chloro-4-methoxyphenol and 1,4-dibromobutane.

EXAMPLE 5

5-[7-(4-Cyanophenoxy)heptyl]-3-methylisoxazole

[I; R is CH$_3$, n is 7, X is O, Ar is 4-NCC$_6$H$_4$], m.p. 56° C., from 3,5-dimethylisoxazole and 6-(4-cyanophenoxy)hexyl bromide; inactive vs. rhinovirus Type 2 in vitro below toxic levels.

The intermediate 6-(4-cyanophenoxy)hexyl bromide was prepared from the potassium salt of 4-cyanophenol and 1,6-dibromohexane.

EXAMPLE 6

5-[6-(4-Cyanophenoxy)hexyl]-3-methylisoxazole

[I; R is CH$_3$, n is 6, X is O, Ar is 4—NCC$_6$H$_4$], m.p. 54° C., white to pale yellow solid, in 49% yield from 3,5-dimethylisoxazole and 5-(4-cyanophenoxy)pentyl bromide; MIC vs. rhinovirus Type 2 in vitro=3.1 μg/ml.

The intermediate 5-(4-cyanophenoxy)pentyl bromide was prepared from the potassium salt of 4-cyanophenol and 1,5-dibromopentane.

EXAMPLE 7

5-[5-(4-Cyanophenoxy)pentyl]-3-methylisoxazole

[I; R is CH$_3$, n is 5, X is O, Ar is 4—NCC$_6$H$_4$], m.p. 60°–61° C., in 43% yield from 3,5-dimethylisoxazole and 4-(4-cyanophenoxy)butyl bromide; inactive vs. rhinovirus Type 2 in vitro below toxic levels.

The intermediate 4-(4-cyanophenoxy)butyl bromide was prepared from the potassium salt of 4-cyanophenol and 1,4-dibromobutane.

EXAMPLE 8

5-[7-(4-Tertiary-butyloxycarbonylphenoxy)heptyl]-3-methylisoxazole

[I; R is CH$_3$, n is 5, X is O, Ar is 4—(CH$_3$)$_3$—COOCC$_6$H$_4$], m.p. 76° C., in 23% yield from 3,5-dimethylisoxazole and 6-(4-tertiary-butyloxycarbonylphenoxy)hexyl bromide; MIC vs. rhinovirus Type 2 in vitro=6.2 μg/ml.

The intermediate 6-(4-tertiary-butyloxycarbonylphenoxy)hexyl bromide was prepared from the potassium salt of 4-(tertiary-butyloxycarbonyl)phenol and 1,6-dibromohexane.

EXAMPLE 9

5-[7-(3-Cyanophenoxy)heptyl]-3-methylisoxazole

[I; R is $CH_3$, n is 7, X is O, Ar is 3-$NCC_6H_4$], m.p. 45° C., in 24% yield from 3,5-dimethylisoxazole and 6-(3-cyanophenoxy)hexyl bromide.

The intermediate 6-(3-cyanophenoxy)hexyl bromide was prepared from the potassium salt of 3-cyanophenol and 1,6-dibromohexane.

EXAMPLE 10

5-[8-(4-Cyanophenoxy)octyl]-3-methylisoxazole

I; R is $CH_3$, n is 8, X is O, Ar is 4-$NCC_6H_4$], pale yellow powder, m.p. 60° C., in 30% yield from 3,5-dimethylisoxazole and 7-(4-cyanophenoxy)heptyl bromide; inactive vs. rhinovirus Type 2 in vitro below toxic levels.

The intermediate 7-(4-cyanophenoxy)heptyl bromide was prepared from the potassium salt of 4-cyanophenol and 1,7-dibromoheptane.

EXAMPLE 11

3-Methyl-5-[7-(4-isopropoxyphenoxy)heptyl]isoxazole

[I; R is $CH_3$, n is 7, X is O, Ar is 4-$(CH_3)_2CHOC_6H_4$], light tan solid, m.p. 38° C., in 30% yield from 3,5-dimethylisoxazole and 6-(4-isopropoxyphenoxy)hexyl bromide; MIC vs. rhinovirus Type 2 in vitro=0.65 μg/ml.

The intermediate 6-(4-isopropoxyphenoxy)hexyl bromide was prepared from the potassium salt of 4-isopropoxyphenol and 1,6-dibromohexane.

EXAMPLE 12

3-Methyl-5-[7-(4-isopropylphenoxy)heptyl]isoxazole

[I; R is $CH_3$, n is 7, X is O, Ar is 4-$(CH_3)_2CHC_6H_4$], viscous yellow liquid, in 70% yield from 3,5-dimethylisoxazole and 6-(4-isopropylphenoxy)hexyl bromide; MIC vs. rhinovirus Type 2 in vitro=0.98 μg/ml.

The intermediate 6-(4-isopropylphenoxy)hexyl bromide was prepared from the potassium salt of 4-isopropylphenol and 1,6-dibromohexane.

EXAMPLE 13

5-[4-(4-Cyanophenoxy)butyl]-3-methylisoxazole

[I; R is $CH_3$, n is 4, X is O, Ar is 4-$NCC_6H_4$], colorless liquid, from 3,5-dimethylisoxazole and 3-(4-cyanophenoxy)propyl bromide.

The intermediate 3-(4-cyanophenoxy)propyl bromide was prepared from the potassium salt of 4-cyanophenol and 1,3-dibromopropane.

EXAMPLE 14

3-Methyl-5-[7-(4-chlorophenoxy)heptyl]isoxazole

[I; R is $CH_3$, n is 7, X is O, Ar is 4-$ClC_6H_4$], colorless solid, m.p. 81° C., from 3,5-dimethylisoxazole and 6-(4-chlorophenoxy)hexyl bromide; MIC vs. rhinovirus Type 2 in vitro=1.5 μg/ml; and vs. polio-2 virus=0.4 μg/ml.

The intermediate 6-(4-chlorophenoxy)hexyl bromide was prepared from the potassium salt of 4-chlorophenol and 1,6-dibromohexane.

EXAMPLE 15

5-[7-(2-Chloro-4-methylphenoxy)heptyl]-3-methylisoxazole

[I; R is $CH_3$, n is 7, X is O, Ar is 2—Cl—4—$CH_3C_6H_3$], amber oil, from 3,5-dimethylisoxazole and 6-(2-chloro-4-methyl)hexyl bromide; MIC vs. rhinovirus Type 2 in vitro=1.2 μg/ml; and vs. polio-2 virus=0.82 μg/ml.

The intermediate 6-(2-chloro-4-methyl)hexyl bromide was prepared from the potassium salt of 2-chloro-4-methylphenol and 1,6-dibromohexane.

By procedures entirely analogous to those described above, it is contemplated that the following compounds can be prepared:

5-[7-(2-Chloro-4-methoxyphenyl)heptyl]-3-methylisoxazole

[I; R is $CH_3$, n is 6, X is $CH_2$, Ar is 2—Cl—4—$CH_3OC_6H_3$], from 3,5-dimethylisoxazole and 6-(2-chloro-4-methoxyphenyl)hexyl iodide (in turn prepared from cyclopropyl methyl ketone and 2-chloro-4-methoxybenzaldehyde according to the procedure described in U.S. Pat. No. 4,093,736).

5-[7-Phenoxyheptyl)-3-methylisoxazole

[I; R is $CH_3$, n is 7, X is O, Ar is $C_6H_5$], from 3,5-dimethylisoxazole and 6-phenoxyhexyl bromide.

5-[7-(2-Chloro-4-methoxyphenoxy)heptyl]-3-ethylisoxazole

I; R is $CH_2CH_3$, n is 7, X is O, Ar is 2—Cl—4—$CH_3OC_6H_3$], from 3-ethyl-5-methylisoxazole and 6-(2-chloro-4-methoxyphenoxy)hexyl bromide.

5-[7-(2-Chloro-4-methoxyphenoxy)heptyl]-3-propylisoxazole

[I; R is $CH_2CH_2CH_3$, n is 7, X is O, Ar is 2—Cl—4—$CH_3OC_6H_3$], from 3-propyl-5-methylisoxazole and 6-(2-chloro-4-methoxyphenoxy)hexyl bromide.

5-[8-(2-Chloro-4-methoxyphenoxy)octyl]-3-methylisoxazole

[I; R is $CH_3$, n is 8, X is O, Ar is 2—Cl—4—$CH_3OC_6H_3$], from 3,5-dimethylisoxazole and 7-(2-chloro-4-methoxyphenoxy)heptyl bromide.

EXAMPLE 16

5-[7-(4-Carboxyphenoxy)heptyl]-3-methylisoxazole

[I; R is $CH_3$, n is 7, X is O, Ar is 4—$HOOCC_6H_4$].

A mixture of 3.0 g (0.01 mole) of 5-[7-(4-cyanophenoxy)heptyl]-3-methylisoxazole (Example 5), 20 ml of 20% aqueous hydrochloric acid and 20 ml of glacial acetic acid was heated at reflux for 19 hours. The reaction mixture was cooled, 20 ml of water added, and the solid product collected by filtration to give 3.0 g of 5-[7-(4-carboxyphenoxy)heptyl]-3-methylisoxazole as a colorless solid, m.p. 129°-130° C.; MIC vs. rhinovirus Type 2 in vitro=10 μg/ml.

The following Examples 17-21 were prepared by procedures analogous to the procedure described in Example 16:

EXAMPLE 17

5-[5-(4-Carboxyphenoxy)pentyl]-3-methylisoxazole

[I; R is $CH_3$, n is 5, X is O, Ar is 4—$HOOCC_6H_4$], m.p. 151° C., in 78% yield from the compound of Example 7; MIC vs. rhinovirus Type 2 in vitro=12.5 μg/ml.

EXAMPLE 18

5-[6-(4-Carboxyphenoxy)hexyl]-3-methylisoxazole

[I; R is $CH_3$, n is 6, X is O, Ar is 4—$HOOCC_6H_4$], m.p. 153°-4° C., in 75% yield from the compound of Example 6.

EXAMPLE 19

5-[7-(3-Carboxyphenoxy)heptyl]-3-methylisoxazole

[I; R is $CH_3$, n is 7, X is O, Ar is 3-$HOOCC_6H_4$], m.p. 95°-96° C., in 80% yield from the compound of Example 9; inactive vs. rhinovirus Type 2 in vitro below toxic levels.

EXAMPLE 20

5-[8-(4-Carboxyphenoxy)octyl]-3-methylisoxazole

[I; R is $CH_3$, n is 8, X is O, Ar is 4—$HOOCC_6H_4$], m.p. 115°-116° C., in 80% yield from the compound of Example 10; inactive vs. rhinovirus Type 2 in vitro below toxic levels.

EXAMPLE 21

5-[4-(4-Carboxyphenoxy)butyl]-3-methylisoxazole

[I; R is $CH_3$, n is 4, X is O, Ar is 4—$HOOCC_6H_4$], m.p. 147°-148° C., in 75% yield from the compound of Example 13.

EXAMPLE 22

5-[7-(4-Ethoxycarbonylphenoxy)heptyl]-3-methylisoxazole

[I; R is $CH_3$, n is 7, X is O, Ar is 4—$EtOOCC_6H_4$].

Hydrogen chloride gas was bubbled through a solution of 5.0 g (0.01 mole) of 5-[7-(4-cyanophenoxy)heptyl]-3-methylisoxazole (Example 5) in 185 ml of absolute ethanol and 0.8 ml of water, heated at reflux for a period of 24 hours. The reaction mixture upon evaporation in vacuo provided 7.0 g of solid residue which was triturated with ether and recrystallized from ethanol. The solid product which separated (1.5 g, m.p. 151° C.) proved to be the corresponding amide (see Example 34). The mother liquors from the recrystallization were concentrated to remove the solvent, and the residue crystallized from ethanol with pentane added to give 1.9 g of 5-[7-(4-ethoxycarbonylphenoxy)heptyl]-3-methylisoxazole, m.p. 60°-61° C.; MIC vs. rhinovirus Type 2 in vitro=0.025 μg/ml.

EXAMPLE 23

5-[5-(4-Ethoxycarbonylphenoxy)pentyl]-3-methylisoxazole

[I; R is $CH_3$, n is 5, X is O, Ar is 4-$EtOOCC_6H_4$].

A mixture of 4.0 g (0.0138 mole) of 5-[5-(4-carboxyphenoxy)pentyl]-3-methylisoxazole (Example 17), 40 ml of absolute ethanol and 0.8 ml of sulfuric acid was heated at reflux for six hours. The solvent was removed in vacuo and the residue made basic with dilute ammonium hydroxide solution. The latter mixture was extracted with ether, and the ether extracts were dried over anhydrous magnesium sulfate and concentrated in vacuo. The residue was dissolved in 30 ml of absolute ethanol, and the solution was evaporated to half volume and diluted with 10 ml of pentane. Upon cooling there separated 2.0 g of 5-[5-(4-ethoxycarbonylphenoxy)pentyl]-3-methylisoxazole, m.p. 50°-51° C.; MIC vs. rhinovirus Type 2 in vitro=0.015 μg/ml.

The following Examples 24-30 were prepared by procedures analogous to the procedure described in Example 23.

EXAMPLE 24

5-[6-(4-Ethoxycarbonylphenoxy)hexyl]-3-methylisoxazole

[I; R is $CH_3$, n is 6, X is O, Ar is 4-$EtOOCC_6H_4$], m.p. 51° C., in 90% yield from 5-[6-(4-carboxyphenoxy)hexyl]-3-methylisoxazole (Example 18); MIC vs. rhinovirus Type 2 in vitro=0.025 μg/ml.

EXAMPLE 25

5-[8-(4-Ethoxycarbonylphenoxy)octyl]-3-methylisoxazole

[I; R is $CH_3$, n is 8, X is O, Ar is 4-$EtOOCC_6H_4$], m.p. 49° C., in 80% yield from 5-[8-(4-carboxyphenoxy)octyl]-3-methylisoxazole (Example 20); MIC vs. rhinovirus Type 2 in vitro=0.05 μg/ml.

EXAMPLE 26

5-[7-(3-Ethoxycarbonylphenoxy)heptyl]-3-methylisoxazole

[I; R is $CH_3$, n is 7, X is O, Ar is 3-$EtOOCC_6H_4$], amber liquid, m.p. 16°-18° C., from 5-[7-(3-carboxyphenoxy)heptyl]-3-methylisoxazole (Example 19); MIC vs. rhinovirus Type 2 in vitro=1.6 μg/ml.

EXAMPLE 27

5-[7-(4-Isopropyloxycarbonylphenoxy)heptyl]-3-methylisoxazole

[I; R is $CH_3$, n is 7, X is O, Ar is 4—$(CH_3)_2CHOOCC_6H_4$], m.p. 45°-46° C., from 5-[7-(4-carboxyphenoxy)heptyl]-3-methylisoxazole (Example 16) and isopropyl alcohol; MIC vs. rhinovirus Type 2 in vitro=0.23 μg/ml.

EXAMPLE 28

5-[7-(4-Propyloxycarbonylphenoxy)heptyl]-3-methylisoxazole

[I; R is $CH_3$, n is 7, X is O, Ar is 4—$CH_3(CH_2)_2OOCC_6H_4$], m.p. 54° C., from 5-[7-(4-carboxyphenoxy)heptyl]-3-methylisoxazole (Example 16) and n-propyl alcohol; MIC vs. rhinovirus Type 2 in vitro=0.07 μg/ml.

EXAMPLE 29

5-[7-(4-Methoxycarbonylphenoxy)heptyl]-3-methylisoxazole

[I; R is $CH_3$, n is 7, X is O, Ar is 4—$CH_3OOCC_6H_4$], m.p. 60° C. in 95% yield from 5-[7-(4-carboxyphenoxy)heptyl]-3-methylisoxazole (Example 16) and methanol; MIC vs. rhinovirus Type 2 in vitro=3 μg/ml.

EXAMPLE 30

5-[4-(4-Ethoxycarbonylphenoxy)butyl]-3-methylisoxazole

[I; R is $CH_3$, n is 4, X is O, Ar is 4—$C_2H_5OOCC_6H_4$], m.p. 61° C. in 90% yield from 5-[4-(4-carboxyphenoxy)- butyl]-3-methylisoxazole (Example 21); MIC vs. rhinovirus Type 2 in vitro=3.1 μg/ml.

EXAMPLE 31

5-[7-(4-Acetylphenoxy)heptyl]-3-methylisoxazole

[I; R is CH₃, n is 7, X is O, Ar is 4—CH₃COC₆H₄].

To a freshly prepared solution of methylmagnesium iodide (from 1.092 g of magnesium and 3.325 ml of methyl iodide in 15 ml of ether) was added dropwise a solution of 8.46 g of 5-[7-(4-cyanophenoxy)heptyl]-3-methylisoxazole (Example 5) in 12 ml of benzene. After the addition was complete, the mixture was heated at reflux for three hours. Saturated ammonium chloride solution (60 ml) was then added with stirring. The water layer was decanted off and the residue treated with 50 ml of dilute hydrochloric acid. The mixture was stirred until complete solution occurred. The aqueous layer was separated and heated at reflux for one hour. The product which separated was collected, dried and recrystallized from ethanol to give 5.23 g of 5-[7-(4-acetylphenoxy)heptyl]-3-methylisoxazole, yellow powder, m.p. 69°–71° C.; MIC vs. rhinovirus Type 2 in vitro=1.6 μg/ml.

EXAMPLE 32

5-[7-(4-Propionylphenoxy)heptyl]-3-methylisoxazole

[I; R is CH₃, n is 7, X is O, Ar is 4—CH₃CH₂COC₆H₄] was prepared from 8.9 g of 5-[7-(4-cyanophenoxy)heptyl]-3-methylisoxazole (Example 5) and ethylmagnesium bromide (from 1.45 g of magnesium and 7.08 g of ethyl bromide) according to the procedure of Example 31. There was obtained 5.7 g of the product with m.p. 61° C. when recrystallized from hexane; MIC vs. rhinovirus Type 2 in vitro=1.7 μg/ml.

EXAMPLE 33

5-[7-(4-Hydrazinocarbonylphenoxy)heptyl]-3-methylisoxazole

[I; R is CH₃, n is 7, X is O, Ar is 4—H₂NNHCOC₆H₄].

A mixture of 3.0 g (0.086 mole) of 5-[7-(4-ethoxycarbonylphenoxy)heptyl]-3-methylisoxazole (Example 22) and 10 ml of hydrazine hydrate was heated at reflux for six hours. The reaction mixture was cooled to 0° C. whereupon the solid product separated. The latter was collected, washed and dried in vacuo to give 2.6 g of 5-[7-(4-hydrazinocarbonylphenoxy)heptyl]-3-methylisoxazole, m.p. 121°–122° C., MIC vs. rhinovirus Type 2 in vitro=0.64 μg/ml.

EXAMPLE 34

5-[7-(4-Carbamylphenoxy)heptyl]-3-methylisoxazole

[I; R is CH₃, n is 7, X is O, Ar is 4—H₂NCOC₆H₄].

A mixture of 4.47 g (0.015 mole) of 5-[7-(4-cyanophenoxy)heptyl]-3-methylisoxazole (Example 5), 8 ml of 30% hydrogen peroxide, 8 ml of 95% ethanol and 0.6 ml of 6 N sodium hydroxide was stirred for ten minutes. There was then added 10 ml of 95% ethanol and the reaction mixture was warmed at 40°–50° C. for 4.5 hours, then held at room temperature overnight and treated with 5% sulfuric acid to neutral pH. The mixture was cooled and the solid product collected by filtration to give 4.4 g of 5-[7-(4-carbamylphenoxy)heptyl]-3-methylisoxazole, m.p. 153°–154° C., and recrystallized from methanol.

5-]7-(4-Carbamylphenoxy)heptyl]-3-methylisoxazole was not active against rhinovirus Type 2 below toxic levels, but is useful as an intermediate in preparing the corresponding ethoxycarbonyl compound (see Example 22) by further hydrolysis and esterification.

EXAMPLE 35

(a)

5-[7-(4-Chlorocarbonylphenoxy)heptyl]-3-methylisoxazole

To a solution of 6.34 g of 5-[7-(4-carbonylphenoxy)heptyl]-3-methylisoxazole (Example 16) in 20 ml of dry benzene was added 10.6 g of thionyl chloride. The mixture was heated at reflux for 90 minutes and then concentrated in vacuo. The residue was dissolved in 30 ml of toluene and again concentrated in vacuo to give 8.0 g of the acid chloride which was used directly in the next reaction without further purification.

(b)

N,N-Dimethyl-4-[7-(3-methyl-5-isoxazolyl)heptyl]benzamide

[I; R is CH₃, n is 7, X is O, Ar is 4—(CH₃)₂NCOC₆H₄].

A solution of 8.0 g of 5-[7-(4-chlorocarbonylphenoxy)heptyl]-3-methylisoxazole in 50 ml of dry toluene was saturated with dimethylamine gas over a 30 minute period. The reaction mixture was concentrated in vacuo, and the residue was dissolved in ether. The ether solution was boiled, treated with petroleum ether until turbid and cooled to produce 6.0 g of N,N-dimethyl-4-[7-(3-methyl-5-isoxazolyl)heptyloxy]benzamide, m.p. 58°–59° C.; MIC vs. polio-2 virus in vitro=2.5 μg/ml.

EXAMPLE 36

5-[7-(4-Propionylphenoxy)heptyl]-3-methylisoxazole oxime

[I; R is CH₃, n is 7, X is O, Ar is 4—CH₃CH₂C(=NOH)C₆H₄].

To a solution of 1.6 g of 5-[7-(4-propionylphenoxy)heptyl]-3-methylisoxazole (Example 32) in 40 ml of ethanol was added a solution of 368 mg of hydroxylamine hydrochloride and 730 mg of sodium acetate in 8 ml of water. The reaction mixture was heated at reflux overnight and then concentrated in vacuo. The residue was recrystallized from aqueous ethanol to give 1.0 g of 5-[7-(4-propionylphenoxy)heptyl]-3-methylisoxazole oxime, colorless solid, m.p. 88°–89° C.; MIC vs. rhinovirus Type 2 in vitro=2.6 μg/ml; and vs. polio-2 virus at 0.2 μg/ml.

EXAMPLE 37

(a)

5-(7-Bromoheptyl)-3-methylisoxazole

[III; R is CH₃, n is 7, Hal is Br].

To a solution of 5.52 g (0.06 mole) of 3,5-dimethylisoxazole in 90 ml of tetrahydrofuran cooled to −70° C. under nitrogen was added over a 10 minute period 37.5 ml (0.06 mole) of butyllithium (1.6 M in hexane). The mixture was stirred 30 minutes at −70° C. and 1.45 g (0.06 mole) of 1,6-dibromohexane in 30 ml of tetrahydrofuran was added over a 75 minute period. The reaction mixture was stirred at −70° C. for one hour, allowed to warm to room temperature and stored in a refrigerator for three days. Concentration of the mixture in vacuo gave an orange oil. The latter was combined with the crude product from another run (0.12 mole) and triturated with 350 ml of methylene dichloride, 200 ml of 5% ammonium chloride solution and 40 ml of dilute hydrochloric acid. The organic layer was separated, dried over anhydrous magnesium sulfate and concentrated in vacuo to give 32.2 g of orange oil. Treatment of the latter with hexane afforded 11.5 g of a solid, m.p. 82° C. which proved to be 1,8-octamethylene-5,5′-bis(3-methylisoxazole). The mother liquors from the latter separation were concentrated and distilled at 90°–100° C.(0.01 mm) to give 3.0 g of 5-(7-bromoheptyl)-3-methylisoxazole as a yellow oil.

(b)

3-Methyl-5-[7-(4-nitrophenyl)heptyl]isoxazole

[I; R is $CH_3$, n is 7, X is O, Ar is 4—$O_2NC_6H_4$].

A mixture of 3.0 g (0.0115 mole) of 5-(7-bromoheptyl)-3-methylisoxazole and 1.85 g (0.0115 mole) of the sodium salt of 4-nitrophenol in 50 ml of dry tetrahydrofuran containing a few crystals of sodium iodide was heated at 80° C. for 24 hours. The reaction mixture was concentrated in vacuo and the residue triturated with 100 ml of methylene dichloride and 40 ml of water. The organic phase was dried and concentrated, and the residue crystallized from ether to give 3.5 g of 3-methyl-5-[7-(4-nitrophenoxy)heptyl]isoxazole, colorless solid, m.p. 58° C.; MIC vs. polio-2 virus in vitro=1.5 µg/ml.

EXAMPLE 38

3-Methyl-5-[7-(2-nitro-4-methoxyphenoxy)heptyl]isoxazole

[I; R is $CH_3$, n is 7, X is O, Ar is 2—$O_2N$—4—$CH_3OC_6H_3$] was prepared from 4.0 g of 5-(7-bromoheptyl)-3-methylisoxazole (Example 37a) and 2.94 g of the sodium salt of 2-nitro-4-methoxyphenol according to the procedure of Example 37, part (b), and was obtained in the form of a yellow solid (4.0 g), m.p. 51° C. when recrystallized from an ether-hexane mixture; MIC vs. rhinovirus Type 2 in vitro=0.3 µg/ml; and vs. polio-2 virus=0.17 µg/ml.

EXAMPLE 39

(a)

4-Cyanophenylvinyl cyclopropyl ketone

To a solution of 39.3 g of 4-cyanobenzaldehyde and 25.2 g of cyclopropyl methyl ketone in 60 ml of absolute ethanol was added 21 ml of 20% sodium hydroxide solution over a 25 minute period. The mixture was stirred for one hour at room temperature, cooled to 1° C. and 40 ml of cold water added. The solid material was collected by filtration and triturated with 450 ml of methylene dichloride and 150 ml of water at room temperature. The aqueous phase was extracted with methylene dichloride and the combined organic layers dried and concentrated in vacuo. The residue was recrystallized from absolute ethanol to give 45.0 g of 4-cyanophenylvinyl cyclopropyl ketone, m.p. 104° C.

(b)

4-Cyanophenylethyl cyclopropyl ketone

A solution of 11.83 g of 4-cyanophenylvinyl cyclopropyl ketone in 200 ml of absolute ethanol containing 0.3 g of 10% palladium-on-carbon catalyst was hydrogenated at an initial pressure of 45 pounds per sq. in. for one hour. The catalyst was filtered off, and the product isolated from the filtrate and recrystallized from methanol to give 8.9 g of 4-cyanophenylethyl cyclopropyl ketone, m.p. 76° C.

(c)

4-Cyanophenylethyl cyclopropyl carbinol

To a solution of 30.9 g of 4-cyanophenylethyl cyclopropyl ketone in 90 ml of absolute ethanol was added 1.48 g of sodium borohydride, and the mixture was stirred at room temperature for three hours. The product isolated from the reaction still contained unreacted starting material, so the material was redissolved in 90 ml of ethanol and treated with 0.7 g additional sodium borohydride for three hours. The product obtained by evaporation of the solvent, trituration of the residue with methylene dichloride and water, and isolation of the product from the organic phase, gave 31.0 g of 4-cyanophenylethyl cyclopropyl carbinol as an oil which crystallized to a colorless solid, m.p. 70°–71° C.

(d)

4-(6-Bromohex-3-enyl)benzonitrile

To a solution of 9.8 g of 4-cyanophenylethyl cyclopropyl carbinol in 140 ml of ether was added 4.24 g of lithium bromide and 3 ml of 2,4,6-collidine. The mixture was cooled to −60° C. and 9.8 g of phosphorus tribromide was added over a five minute period. The reaction mixture was allowed to warm to 0° C., kept at that temperature for two hours and then allowed to warm to 18° C. Collidine (18 ml) was added, and after 15 minutes of stirring, the mixture was poured into 200 ml of water and 100 ml of ether. The ether extracts were washed with dilute aqueous sulfuric acid and water, dried over anhydrous magnesium sulfate and concentrated to a volume of 150 ml. Zinc bromide (11.6 g) was then added with cooling, and the mixture was stirred at room temperature for 29 hours. The ether solution was washed with water, dried and concentrated to give 12.5 g of 4-(6-bromohex-3-enyl)benzonitrile as a yellow oil.

(e)

4-(6-Bromohexyl)benzonitrile

A solution of 10.5 g of 4-(6-bromohex-3-enyl)benzonitrile in 200 ml of absolute ethanol was hydrogenated in the presence of 0.25 g of platinum oxide catalyst. Isolation of the product afforded 10.4 g of 4-(6-bromohexyl)benzonitrile as a yellow oil which was distilled at 168°–170° C. (0.01 mm) to produce the compound as a colorless oil which solidified upon cooling.

(f)

5-[7-(4-Cyanophenyl)heptyl]-3-methylisoxazole

[I; R is $CH_3$, n is 6, X is $CH_2$, Ar is 4—$NCC_6H_4$] was prepared from 4-(6-bromohexyl)benzonitrile and the lithium derivative of 3,5-dimethylisoxazole according to the procedure of Example 1. The crude product was chromatographed on magnesium silicate (Florisil) using the solvent series hexane:ether:methanol for elution. Ether-hexane 30:70 and 40:60 brought out the desired 5-[7-(4-cyanohexyl)heptyl]-3-methylisoxazole, obtained as a colorless solid, m.p. 61° C., when recrystallized from ether; MIC vs. rhinovirus Type 2 in vitro=11.2 µg/ml.

5-[7-(4-cyanophenyl)heptyl]-3-methylisoxazole and related compounds of Formulas I and II where Ar is 4-cyanophenyl are disclosed as intermediates in copending application Ser. No. 527,583, filed Aug. 29, 1983.

EXAMPLE 40

(a)

3-Hydroxymethyl-5-methylisoxazole was prepared from 93.4 g of methyl 5-methylisoxazole-3-carboxylate and 62.5 g of sodium borohydride in 1200 ml of t-butyl alcohol and 600 ml of methanol. Isolation of the product and distillation gave 59.2 g of 3-hydroxymethyl-5-methylisoxazole, b.p. 68°–70° C.(0.05 mm).

(b)

3-Chloromethyl-5-methylisoxazole

To a solution of 119.6 g of 3-hydroxymethyl-5-methylisoxazole in 600 ml of ether was slowly added 155 ml of thionyl chloride in 200 ml of ether over a five hour period. The solution was concentrated to an oily residue which was distilled to give 121.2 g of 3-chloromethyl-5-methylisoxazole, b.p. 70°–71° C.(11 mm).

(c)

5-Methyl-3-isoxazolepropanoic acid

To a stirred suspension of 78.5 g of sodium hydride in 1 liter of tetrahydrofuran under nitrogen was added in portions 261 g of diethyl malonate. When evolution of hydrogen had ceased, 108 g of 3-chloromethyl-5-methylisoxazole was added and the reaction mixture was heated at reflux for four hours. A portion of the tetrahydrofuran (800 ml) was distilled off and 1 liter of 5% sodium hydroxide solution was added to the remaining mixture which was then heated at reflux for three hours and allowed to stand at room temperature for three days. The reaction mixture was filtered and the filtrate extracted with hexane. The aqueous layer was acidified with concentrated hydrochloric acid and extracted repeatedly with ethyl acetate. The ethyl acetate was removed in vacuo, 100 ml of pyridine added to the residue, and the mixture heated at reflux for three hours until evolution of carbon dioxide ceased. The mixture was concentrated in vacuo and the residue acidified with 6 N hydrochloride acid and cooled. The solid which separated was collected and dissolved in methylene dichloride. The layers were separated and the methylene dichloride layer concentrated in vacuo. The residual solid was slurried with isopropyl acetate—hexane to give 75.4 g of 5-methyl-3-isoxazole-propanoic acid, m.p. 82°–84° C.

(d)

Methyl 5-methyl-3-isoxazolepropanoate

A mixture of 75.4 g of 5-methyl-3-isoxazolepropanoic acid, 150 ml of boron trifluoride etherate and 400 ml of methanol was heated at reflux for eight hours. The reaction mixture was concentrated in vacuo, made basic with sodium bicarbonate solution and extracted with methylene dichloride. The extracts were concentrated in vacuo and the residue distilled at 90°–100° C.(0.05 mm) to give 73 g of methyl 5-methyl-3-isoxazole-propanoate which crystallized to a solid, m.p. 54°–55° C.

(e)

5-Methyl-3-(3-hydroxypropyl)isoxazole

To a suspension of 7.6 g of lithium aluminum hydride in 250 ml of tetrahydrofuran was added a solution of 64.9 g of methyl 5-methyl-3-isoxazolepropanoate in 100 ml of tetrahydrofuran. The reaction mixture was stirred at reflux for three hours, then cooled and 15.2 ml of water in 30 ml of tetrahydrofuran added. The mixture was filtered and the filtrate concentrated in vacuo. The residue was distilled to give 44.1 g of 5-methyl-3-(3-hydroxypropyl)isoxazole, b.p. 84°–85° C.(0.1 mm).

(f)

5-Methyl-3-(3-bromopropyl)isoxazole

Bromine (33.8 g) was added to a suspension of 55.5 g of triphenylphosphine in 400 ml of acetonitrile. The mixture was stirred for 30 minutes and concentrated in vacuo to remove the solvent. To the residue was added 200 ml of dimethylformamide, and with stirring 29.8 g of 5-methyl-3-(3-hydroxypropyl)isoxazole was added. An exothermic reaction ensued and the solid materials dissolved to form an orange solution which was poured into water and extracted with methylene dichloride. The methylene dichloride extracts were concentrated and the residue distilled to give 34.1 g of 5-methyl-3-(3-bromopropyl)isoxazole, b.p. 115°–125° C.(0.05 mm).

(g)

3-(4-Carboxybutyl)-5-methylisoxazole was prepared from 5-methyl-3-(3-bromopropyl)isoxazole and diethyl malonate according to the procedure of part (c) above, and was obtained in 56% yield as a colorless solid, m.p. 58°–60° C. when recrystallized from carbon tetrachloride.

(h)

3-(5-Hydroxypentyl)-5-methylisoxazole was prepared by reduction of 3-(4-carboxybutyl)-3-methylisoxazole with lithium aluminum hydride according to the procedure of part (e) above, and was obtained in 84% yield as an oil, b.p. 115°–125° C.(0.1 mm).

(i)

3-(5-Bromopentyl)-5-methylisoxazole was prepared by reacting 3-(5-hydroxypentyl)-5-methylisoxazole with bromine and triphenylphosphine according to the procedure of part (f) above, and was obtained in 77% yield as an oil, b.p. 140°–150° C.(0.05 mm).

(j)

3-[5-(4-Cyanophenoxy)pentyl]-5-methylisoxazole

[II; R is $CH_3$, n is 5, Ar is 4—$NCC_6H_4$].

A mixture of 5.1 g of 4-cyanophenol, 10 g of 3-(5-bromopentyl)-5-methylisoxazole, 8 g of potassium carbonate, 1 g of potassium iodide and 75 ml of acetonitrile was heated at reflux for 24 hours. The product was isolated and distilled, first at 115°–200° C.(0.1 mm) and then at 160°–190° C. (0.05 mm) to yield a yellow oil which crystallized upon cooling. Recrystallization fron hexane—ether afforded 6.2 g of 3-[5-(4-cyanophenoxy)-pentyl]-5-methylisoxazole, m.p. 61°–62° C.

EXAMPLE 41

3-[5-(2-Chloro-4-methoxyphenoxy)pentyl]-5-methylisoxazole

[II; R is $CH_3$, n is 5, Ar is 2—Cl—4—$CH_3OC_6H_3$].

A mixture of 5.5 g (0.0345 mole) of 2-chloro-4-methoxyphenol, 8.0 g (0.0345 mole) of 3-(5-bromopentyl)-5-methylisoxazole (Example 40i), 6 g of potassium carbonate, 0.1 g of potassium iodide and 75 ml of acetonitrile was heated at reflux for 24 hours. The reaction mixture was filtered, concentrated in vacuo, dissolved in 50 ml of methylene dichloride, filtered and again concentrated. The residue was distilled at 135°–200° C.(0.2 mm) and then redistilled, collecting the fraction boiling at 170°–190° C.(0.05 mm). The product crystallized and was recrystallized from ether—pentane to give 5.2 g of 3-[5-(2-chloro-4-methoxyphenoxy)pentyl]-5-methylisoxazole, m.p. 45°–47° C.; MIC vs. rhinovirus Type 2=0.7 μg/ml; and vs. polio-2 virus=1.4 μg/ml.

I claim:

1. A compound having the formula

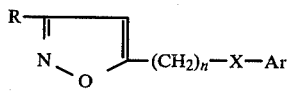

or

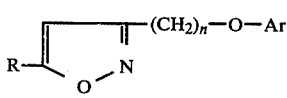

wherein:
R is alkyl of 1 to 3 carbon atoms;
X is O or CH$_2$;
n is an integer from 4 to 8; and
Ar is phenyl or phenyl substituted by one or two substituents selected from the group consisting of halogen, lower-alkyl, lower-alkoxy, nitro, cyano, carboxy, lower-alkoxycarbonyl, lower-alkanoyl, 1-oximino-lower-alkyl, hydrazinocarbonyl, carbamyl and N,N-di-lower-alkylcarbamyl.

2. A compound according to claim 1 having the formula

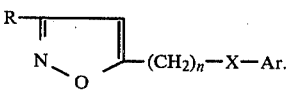

3. A compound according to claim 2 where X is O, R is CH$_3$ and Ar is 2-chloro-4-methoxyphenyl.

4. 5-[7-(2-Chloro-4-methoxyphenoxy)heptyl]-3-methylisoxazole, according to claim 3.

5. 5-[6-(2-Chloro-4-methoxyphenoxy)hexyl]-3-methylisoxazole, according to claim 3.

6. 5-[5-(2-Chloro-4-methoxyphenoxy)pentyl]-3-methylisoxazole, according to claim 3.

7. A compound according to claim 2 wherein X is O, R is CH$_3$ and Ar is lower-alkoxycarbonylphenyl.

8. 5-[7-(4-Ethoxycarbonylphenoxy)heptyl]-3-methylisoxazole, according to claim 7.

9. 5-[5-(4-Ethoxycarbonylphenoxy)pentyl]-3-methylisoxazole, according to claim 7.

10. 5-[6-(4-Ethoxycarbonylphenoxy)hexyl]-3-methylisoxazole, according to claim 7.

11. 5-[8-(4-Ethoxycarbonylphenoxy)octyl]-3-methylisoxazole, according to claim 7.

12. 5-[7-(4-Isopropyloxycarbonylphenoxy)heptyl]-3-methylisoxazole, according to claim 7.

13. 5-[7-(4-Propyloxycarbonylphenoxy)heptyl]-3-methylisoxazole, according to claim 7.

14. A compound according to claim 1 having the formula

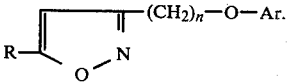

15. A compound according to claim 14 wherein R is methyl and Ar is 2-chloro-4-methoxyphenyl.

16. 3-[5-(2-Chloro-4-methoxyphenoxy)pentyl]-5-methylisoxazole, according to claim 15.

17. A composition for combatting viruses which comprises an antivirally effective amount of at least one compound according to claim 1 in admixture with a suitable carrier or diluent.

18. A composition according to claim 17 wherein the antivirally effective compound is 5-[7-(2-chloro-4-methoxyphenoxy)heptyl]-3-methylisoxazole.

19. A method for combatting viruses which comprises contacting the locus of said viruses with a composition according to claim 17.

20. A method according to claim 19 wherein said composition contains as the antivirally effective compound 5-[7-(2-chloro-4-methoxyphenoxy)heptyl]-3-methylisoxazole.

* * * * *

UNITED STATES PATENT AND TRADEMARK OFFICE
CERTIFICATE OF CORRECTION

PATENT NO. : 4,451,476
DATED : May 29, 1984
INVENTOR(S) : Guy D. Diana

It is certified that error appears in the above-identified patent and that said Letters Patent is hereby corrected as shown below:

Column 3, line 29, "$n$-" should read --$n$-1--.

Column 6, lines 9-10, "2-Cl-4-$CH_3OC_6H$" should read --2-Cl-4-$CH_3OC_6H_3$--.

Column 12, line 10, "(4-carbonylphenoxy)-" should read --(4-carboxyphenoxy)- --; line 20, "heptyl]" should read --heptyloxy]--.

Column 13, line 14, "(4-nitrophenyl)" should read --(4-nitrophenoxy)--.

Column 15, line 42, "hydrochloride acid" should read --hydrochloric acid--.

Signed and Sealed this

Twenty-seventh Day of November 1984

[SEAL]

Attest:

GERALD J. MOSSINGHOFF

Attesting Officer     Commissioner of Patents and Trademarks